(12) United States Patent
Kusens

(10) Patent No.: US 10,546,481 B2
(45) Date of Patent: *Jan. 28, 2020

(54) METHOD FOR DETERMINING WHETHER AN INDIVIDUAL LEAVES A PRESCRIBED VIRTUAL PERIMETER

(71) Applicant: CERNER INNOVATION, INC., Kansas City, KS (US)

(72) Inventor: Neil Kusens, Sherman Oaks, CA (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/872,564

(22) Filed: Jan. 16, 2018

(65) Prior Publication Data

US 2018/0144605 A1 May 24, 2018

Related U.S. Application Data

(63) Continuation of application No. 15/279,054, filed on Sep. 28, 2016, now Pat. No. 9,905,113, which is a
(Continued)

(51) Int. Cl.
*A61B 5/00* (2006.01)
*G08B 21/22* (2006.01)
(Continued)

(52) U.S. Cl.
CPC ............ *G08B 21/22* (2013.01); *A61B 5/1115* (2013.01); *G06K 9/00201* (2013.01);
(Continued)

(58) Field of Classification Search
CPC .... G08B 21/02; G08B 21/18; G08B 13/2462; G08B 21/0202; A01K 11/006;
(Continued)

(56) References Cited

U.S. PATENT DOCUMENTS 1,860,487 A 5/1932 Alfred et al.
4,669,263 A 6/1987 Sugiyama
(Continued)

FOREIGN PATENT DOCUMENTS

DE 19844918 A1 4/2000
WO 2007/081629 A2 7/2007
(Continued)

OTHER PUBLICATIONS

US 9,948,899 B1, 04/2018, Kusens (withdrawn)
(Continued)

*Primary Examiner* — Kerri L McNally
(74) *Attorney, Agent, or Firm* — Shook, Hardy & Bacon, LLP

(57) ABSTRACT

A method and system that allows healthcare providers, hospitals, skilled nursing facilities and other persons to monitor disabled, elderly or other high-risk individuals to prevent or reduce falls and/or mitigate the impact of a fall by delivering automated notification of "at risk" behavior and falls by such an individual being monitored where assistance is required.

20 Claims, 15 Drawing Sheets

Related U.S. Application Data continuation of application No. 14/728,762, filed on Jun. 2, 2015, now Pat. No. 9,489,820, which is a continuation-in-part of application No. 14/084,588, filed on Nov. 19, 2013, now Pat. No. 9,159,215, which is a continuation-in-part of application No. 13/543,816, filed on Jul. 7, 2012, now Pat. No. 9,129,506.

(60) Provisional application No. 61/507,088, filed on Jul. 12, 2011, provisional application No. 61/798,964, filed on Mar. 15, 2013.

(51) Int. Cl.
| | |
|---|---|
| *G06K 9/00* | (2006.01) |
| *G06K 9/20* | (2006.01) |
| *G08B 3/10* | (2006.01) |
| *G08B 21/04* | (2006.01) |
| *G08B 25/00* | (2006.01) |
| *G08B 25/14* | (2006.01) |
| *A61B 5/11* | (2006.01) |

(52) U.S. Cl.
CPC ...... *G06K 9/00342* (2013.01); *G06K 9/00362* (2013.01); *G06K 9/00771* (2013.01); *G06K 9/2081* (2013.01); *G08B 3/10* (2013.01); *G08B 21/043* (2013.01); *G08B 21/0423* (2013.01); *G08B 21/0469* (2013.01); *G08B 21/0476* (2013.01); *G08B 25/001* (2013.01); *G08B 25/14* (2013.01); *A61B 5/1128* (2013.01); *A61B 5/746* (2013.01); *A61B 2503/08* (2013.01)

(58) Field of Classification Search
CPC ... A61B 5/0022; A61B 5/0024; A61B 5/1117; G01S 5/0027
USPC ........................................................ 340/573.4
See application file for complete search history.

(56) References Cited

U.S. PATENT DOCUMENTS

| | | | |
|---|---|---|---|
| 4,857,716 A | 8/1989 | Gombrich et al. | |
| 5,031,228 A | 7/1991 | Lu | |
| 5,276,432 A | 1/1994 | Travis | |
| 5,448,221 A * | 9/1995 | Weller | G08B 21/22 |
| | | | 340/539.21 |
| 5,482,050 A | 1/1996 | Smokoff et al. | |
| 5,592,153 A | 1/1997 | Welling et al. | |
| 5,798,798 A | 8/1998 | Rector et al. | |
| 5,838,223 A | 11/1998 | Gallant et al. | |
| 5,915,379 A | 6/1999 | Wallace et al. | |
| 5,942,986 A | 8/1999 | Shabot et al. | |
| 6,050,940 A | 4/2000 | Braun et al. | |
| 6,095,984 A | 8/2000 | Amano et al. | |
| 6,160,478 A | 12/2000 | Jacobsen et al. | |
| 6,174,283 B1 | 1/2001 | Nevo et al. | |
| 6,188,407 B1 | 2/2001 | Smith et al. | |
| 6,269,812 B1 | 8/2001 | Wallace et al. | |
| 6,287,452 B1 | 9/2001 | Allen et al. | |
| 6,322,502 B1 | 11/2001 | Schoenberg et al. | |
| 6,369,838 B1 | 4/2002 | Wallace et al. | |
| 6,429,869 B1 | 8/2002 | Kamakura et al. | |
| 6,614,349 B1 * | 9/2003 | Proctor | G08B 13/1427 |
| | | | 340/5.92 |
| 6,727,818 B1 | 4/2004 | Wildman et al. | |
| 6,804,656 B1 | 10/2004 | Rosenfeld et al. | |
| 7,015,816 B2 | 3/2006 | Wildman et al. | |
| 7,122,005 B2 | 10/2006 | Shusterman | |
| 7,154,397 B2 | 12/2006 | Zerhusen et al. | |
| 7,237,287 B2 | 7/2007 | Weismiller et al. | |
| 7,323,991 B1 | 1/2008 | Eckert et al. | |
| 7,408,470 B2 | 8/2008 | Wildman et al. | |
| 7,420,472 B2 | 9/2008 | Tran | |
| 7,430,608 B2 | 9/2008 | Noonan et al. | |
| 7,502,498 B2 | 3/2009 | Wen et al. | |
| 7,612,679 B1 | 11/2009 | Fackler et al. | |
| 7,669,263 B2 | 3/2010 | Menkedick et al. | |
| 7,715,387 B2 | 5/2010 | Schuman | |
| 7,724,147 B2 | 5/2010 | Brown | |
| 7,756,723 B2 | 7/2010 | Rosow et al. | |
| 7,890,349 B2 | 2/2011 | Cole et al. | |
| 7,893,842 B2 | 2/2011 | Deutsch | |
| 7,895,055 B2 | 2/2011 | Schneider et al. | |
| 7,908,153 B2 | 3/2011 | Scherpbier et al. | |
| 7,945,457 B2 | 5/2011 | Zaleski | |
| 7,962,544 B2 | 6/2011 | Torok et al. | |
| 7,972,140 B2 | 7/2011 | Renaud | |
| 8,108,036 B2 | 1/2012 | Tran | |
| 8,123,685 B2 | 2/2012 | Brauers et al. | |
| 8,128,596 B2 | 3/2012 | Carter | |
| 8,224,108 B2 | 7/2012 | Steinberg et al. | |
| 8,237,558 B2 | 8/2012 | Seyed Momen et al. | |
| 8,273,018 B1 | 9/2012 | Fackler et al. | |
| 8,432,263 B2 | 4/2013 | Kunz | |
| 8,451,314 B1 | 5/2013 | Cline et al. | |
| 8,529,448 B2 | 9/2013 | McNair | |
| 8,565,500 B2 | 10/2013 | Neff | |
| 8,620,682 B2 | 12/2013 | Bechtel et al. | |
| 8,655,680 B2 | 2/2014 | Bechtel et al. | |
| 8,700,423 B2 | 4/2014 | Eaton, Jr. et al. | |
| 8,727,961 B2 | 5/2014 | Ziv | |
| 8,727,981 B2 | 5/2014 | Bechtel et al. | |
| 8,769,153 B2 | 7/2014 | Dziubinski | |
| 8,890,937 B2 | 11/2014 | Skubic et al. | |
| 8,902,068 B2 | 12/2014 | Bechtel et al. | |
| 8,917,186 B1 | 12/2014 | Grant | |
| 8,953,886 B2 | 2/2015 | King et al. | |
| 9,072,929 B1 | 7/2015 | Rush et al. | |
| 9,129,506 B1 | 9/2015 | Kusens | |
| 9,147,334 B2 | 9/2015 | Long et al. | |
| 9,159,215 B1 * | 10/2015 | Kusens | G08B 21/22 |
| 9,269,012 B2 | 2/2016 | Fotland | |
| 9,292,089 B1 | 3/2016 | Sadek | |
| 9,305,191 B2 | 4/2016 | Long et al. | |
| 9,330,987 B2 | 5/2016 | Lin et al. | |
| 9,408,561 B2 | 8/2016 | Stone et al. | |
| 9,489,820 B1 * | 11/2016 | Kusens | A61B 5/746 |
| 9,519,215 B2 | 12/2016 | Robinson et al. | |
| 9,519,969 B1 | 12/2016 | Kusens | |
| 9,524,443 B1 | 12/2016 | Kusens | |
| 9,536,310 B1 | 1/2017 | Kusens | |
| 9,538,158 B1 | 1/2017 | Rush et al. | |
| 9,563,955 B1 | 2/2017 | Kamarshi et al. | |
| 9,597,016 B2 | 3/2017 | Stone et al. | |
| 9,729,833 B1 | 8/2017 | Kusens | |
| 9,741,227 B1 | 8/2017 | Kusens | |
| 9,892,310 B2 | 2/2018 | Kusens et al. | |
| 9,892,311 B2 | 2/2018 | Kusens et al. | |
| 9,892,611 B1 | 2/2018 | Kusens | |
| 9,905,113 B2 * | 2/2018 | Kusens | A61B 5/746 |
| 10,078,956 B1 | 9/2018 | Kusens | |
| 10,090,068 B2 | 10/2018 | Kusens et al. | |
| 10,091,463 B1 * | 10/2018 | Kusens | G06K 9/46 |
| 10,096,223 B1 | 10/2018 | Kusens | |
| 10,225,522 B1 | 3/2019 | Kusens | |
| 2002/0015034 A1 | 2/2002 | Malmborg | |
| 2002/0038073 A1 | 3/2002 | August | |
| 2002/0077863 A1 | 6/2002 | Rutledge et al. | |
| 2002/0101349 A1 | 8/2002 | Rojas, Jr. | |
| 2002/0115905 A1 | 8/2002 | August | |
| 2002/0183976 A1 | 12/2002 | Pearce | |
| 2003/0037786 A1 | 2/2003 | Biondi et al. | |
| 2003/0070177 A1 | 4/2003 | Kondo et al. | |
| 2003/0092974 A1 | 5/2003 | Santoso et al. | |
| 2003/0095147 A1 | 5/2003 | Daw | |
| 2003/0135390 A1 | 7/2003 | O'Brien et al. | |
| 2003/0140928 A1 | 7/2003 | Bui et al. | |
| 2003/0227386 A1 | 12/2003 | Pulkkinen et al. | |
| 2004/0019900 A1 | 1/2004 | Knightbridge et al. | |
| 2004/0052418 A1 | 3/2004 | DeLean | |

(56) References Cited

U.S. PATENT DOCUMENTS

| | | |
|---|---|---|
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1* | 12/2007 | Warriner ............... G07C 11/00 340/539.23 |
| 2007/0296600 A1 | 12/2007 | Dixon et al. |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 | 1/2008 | Rodgers |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0236132 A1 | 10/2008 | Molnar |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins, Jr. et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1* | 11/2009 | Ecker ............... G06K 9/00348 348/152 |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1* | 4/2011 | Aarts ............... A61B 7/003 600/300 |
| 2011/0087125 A1 | 4/2011 | Causevic |
| 2011/0087707 A1 | 4/2011 | Abraham |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0245707 A1 | 10/2011 | Castle et al. |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Tenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0191861 A1 | 7/2014 | Scherrer |
| 2014/0213845 A1 | 7/2014 | Bechtel et al. |
| 2014/0267625 A1 | 9/2014 | Clark et al. |
| 2014/0267736 A1 | 9/2014 | Delean |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0109442 A1 | 4/2015 | Derenne et al. |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1 | 1/2016 | Hayes et al. |
| 2016/0070869 A1 | 3/2016 | Portnoy |
| 2016/0093195 A1 | 3/2016 | Ophardt |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0091562 A1 | 3/2017 | Kusens |
| 2017/0109991 A1 | 4/2017 | Kusens |
| 2017/0143240 A1 | 5/2017 | Stone et al. |
| 2017/0193177 A1 | 7/2017 | Kusens |
| 2017/0193279 A1 | 7/2017 | Kusens et al. |
| 2017/0193772 A1 | 7/2017 | Kusens et al. |
| 2017/0195637 A1 | 7/2017 | Kusens et al. |

(56) References Cited

U.S. PATENT DOCUMENTS

| | | |
|---|---|---|
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0114053 A1 | 4/2018 | Kusens et al. |
| 2018/0137340 A1 | 5/2018 | Kusens et al. |
| 2018/0189946 A1 | 7/2018 | Kusens et al. |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0122028 A1 | 4/2019 | Kusens et al. |

FOREIGN PATENT DOCUMENTS

| | | |
|---|---|---|
| WO | 2009018422 A1 | 2/2009 |
| WO | 2012122002 A1 | 9/2012 |

OTHER PUBLICATIONS

Raheja, et al., "Human Facial Expression Detection From Detected in CapturedImage Using Back Propagation Neural Network", International Journal of Computer Science and Information Technology (IJCSIT), vol. 2, No. 1, Feb. 2010, 8 pages.

Tom Mooney, "Rhode Island ER first to test Google Glass on medical conditions", http://www.ems1.com/ems-products/cameras-video/articles/1860487-Rhode-Island-ER-first printed on Mar. 11, 2014.

Final Office Action dated Dec. 12, 2017 in U.S. Appl. No. 14/575,850, 10 pages.

First Action Interview Office Action dated Nov. 28, 2017 in U.S. Appl. No. 14/244,160, 5 pages.

Non-Final Office Action dated Apr. 14, 2017 in U.S. Appl. No. 15/396,263, 18 pages.

Notice of Allowance dated Dec. 29, 2017 in U.S. Appl. No. 14/611,363, 11 pages.

Notice of Allowance dated Dec. 6, 2017 in U.S. Appl. No. 15/395,716, 5 pages.

Notice of Allowance dated Nov. 27, 2017 in U.S. Appl. No. 15/279,054, 2 pages.

Final Office Action dated Feb. 16, 2018 in U.S. Appl. No. 14/757,593, 8 pages.

First Action Interview Office Action dated Feb. 22, 2018 in U.S. Appl. No. 15/134,189, 4 pages.

First Action Interview Pre-Interview Communication dated May 21, 2018 in U.S. Appl. No. 15/910,645, 14 pages.

Non-Final Office Action dated Feb. 22, 2018 in U.S. Appl. No. 14/599,498, 24 pages.

Non-Final Office Action dated Feb. 7, 2018 in U.S. Appl. No. 15/396,263, 19 pages.

Non-Final Office Action dated Mar. 12, 2018 in U.S. Appl. No. 15/285,416, 20 pages.

Non-Final Office Action dated Mar. 14, 2018 in U.S. Appl. No. 14/757,877, 13 pages.

Non-Final Office Action dated May 2, 2018 in U.S. Appl. No. 15/728,110, 8 pages.

Non-Final Office Action dated May 31, 2018 in U.S. Appl. No. 15/395,762, 24 pages.

Non-Final Office Action dated May 31, 2018 in U.S. Appl. No. 15/848,621, 23 pages.

Non-Final Office Action dated May 7, 2018 in U.S. Appl. No. 14/611,363, 6 pages.

Non-Final Office Action dated May 8, 2018 in U.S. Appl. No. 15/148,151, 5 pages.

Notice of Allowance dated Feb. 12, 2018 in U.S. Appl. No. 14/623,349, 12 pages.

Notice of Allowance dated Jan. 18, 2018 in U.S. Appl. No. 15/279,054, 2 pages.

Notice of Allowance dated May 9, 2018 in U.S. Appl. No. 15/395,716, 5 pages.

Virtual Patient Observation: Centralize Monitoring of High-Risk Patients with Video—Cisco Video Surveillance Manager, https://www.cisco.com/c/en/us/products/collateral/physical-security/video-surveillance-manager/white paper_ C11-715263.pdf.

Non-Final Office Action dated Jun. 8, 2018 in U.S. Appl. No. 15/628,318, 9 new pages.

Notice of Allowance dated Jun. 13, 2018 in U.S. Appl. No. 14/575,850, 5 pages.

Notice of Allowance dated Jun. 18, 2018 in U.S. Appl. No. 14/623,349, 11 pages.

Notice of Allowance dated Jun. 19, 2018 in U.S. Appl. No. 15/395,716, 2 pages.

Final Office Action dated Jul. 5, 2018 in U.S. Appl. No. 15/285,416, 8 pages.

Final Office Action dated Jul. 12, 2018 in U.S. Appl. No. 15/134,189, 23 pages.

Notice of Allowance dated Jul. 13, 2018 in U.S. Appl. No. 15/396,263, 9 pages.

Notice of Allowance dated Jul. 18, 2018 in U.S. Appl. No. 14/599,498, 6 pages.

Notice of Allowance dated Jul. 23, 2018 in U.S. Appl. No. 15/728,110, 15 pages.

Non-Final Office Action dated Aug. 15, 2018 in U.S. Appl. No. 15/910,632, 7 pages.

Non Final Office Action received for U.S. Appl. No. 15/395,243, dated Feb. 14, 2019, 14 pages.

Non Final Office Action received for U.S. Appl. No. 16/107,567, dated Mar. 29, 2019, 8 pages.

Non-Final Office Action received for U.S. Appl. No. 15/134,189, dated May 9, 2019, 30 pages.

Non-Final Office Action received for U.S. Appl. No. 15/395,762, dated May 1, 2019, 27 pages.

Non-Final Office Action received for U.S. Appl. No. 15/856,419, dated May 2, 2019, 8 pages.

Preinterview first office action received for U.S. Appl. No. 15/857,696, dated May 23, 2019, 14 pages.

Conaire et al., "Fusion of infrared and visible spectrum video for indoor surveillance", WIAMIS, Apr. 2005, 4 pages.

* cited by examiner

/ - Virtual Safety Rail

△ - Bed Zone

△ - Auto Bed Zone (Select Patient)

⊞ - Auto Bed Zone (Auto-select)

▯▾ - Saved Zones

☐ - Clear All

METHOD FOR DETERMINING WHETHER AN INDIVIDUAL LEAVES A PRESCRIBED VIRTUAL PERIMETER

This application is a continuation of U.S. application Ser. No. 15/279,054, filed Sep. 28, 2016, which is a continuation of U.S. application Ser. No. 14/728,762, filed Jun. 2, 2015, which is a continuation-in-part of U.S. application Ser. No. 14/084,588, filed Nov. 19, 2013, which is a continuation-in-part of U.S. application Ser. No. 13/543,816, filed Jul. 7, 2012, which claimed priority to and the benefit of U.S. Application Ser. No. 61/507,088, filed Jul. 12, 2011. U.S. application Ser. No. 14/728,762 also claims priority to and the benefit of U.S. Application Ser. No. 61/798,964, filed Mar. 15, 2013. All of the above applications are hereby incorporated by reference in their entireties.

1. FIELD OF THE DISCLOSURE

The present disclosure is generally directed to patient monitoring systems and particularly to a system and method for monitoring patients in a manner which prevents or reduces patient falls.

2. BACKGROUND

According to recent studies, falls are a leading cause of death among people over the age of 65 years and 10% of the fatal falls for patients over 65 years of age occur in a hospital setting. For the general population, studies estimate that patient falls occur in 1.9 to 3% of all acute care hospitalizations. Of these hospital-based falls, approximately 30% will result in a serious injury with the cost to care for these injuries estimated to reach $54.9 billion per year by 2020. Current technologies that exist to assist in the prevention of falls are limited in their capabilities. These include pressure pads on the bed that trigger an alert when no pressure is detected on the pad, pressure pads on the floor and light beams that create a perimeter with alarms going off upon interruption of the beam. The pressure pads are ineffective as they do not prevent the fall but rather alert after the fact when it is too late. Additionally they are prone to false positive alerts. The light beams are also prone to false alerts when the patient or visitor simply reaches through it or the caregiver breaks the beam while delivering medication, food, drink or conducting a procedure on the patient.

SUMMARY OF THE DISCLOSURE

The present disclosure is directed to addressing these above-described shortcomings with current technology. Generally disclosed is a novel method and system that allows healthcare providers, hospitals, skilled nursing facilities and other persons to monitor disabled, elderly or other high-risk individuals and utilize the described technology to prevent or reduce falls and/or mitigate the impact of a fall by delivering automated notification of "at risk" behavior and falls by such an individual being monitored where assistance is required.

The following non-limiting definitions are provided as aid in understanding the disclosed novel method and system:

| | |
|---|---|
| 3D Camera, Motion and Sound Sensor | An electronic device that contains one or more cameras capable of identifying individual objects, people and motion regardless of lighting conditions as well as one or more microphones to detect audio. The cameras can utilize technologies including but not limited to color RGB, CMOS sensors, infrared projectors and RF-modulated light. They may also contain microprocessors and image sensors to detect and process information both sent out and received by the various cameras. |
| | The electronic device calculates if there has been a change in location of the person or object of interest over a period of time. As a non-limiting example, a person's right knee can be at time T1 located at coordinates (x1, y1, z1) in a picture frame taken by the camera. At time T2 the right knee is capture by the picture frame taken by the camera at coordinates (x2, y2, z2). Based on this information, motion, speed and direction can be derived utilizing the elapsed time and comparing the two 3D coordinates over the elapsed time, As opposed to conventional motion sensors, which use captured motion to control a camera, the 3D Motion and Sound Sensor used with the method and system, uses the camera in order to compute the motion. The camera/sensors are preferably continuously on at all times while the monitoring is occurring, regardless of whether the person or object of interest is moving or not. |
| | The 3D Camera, Motion and Sound sensor can additionally be programmed to lock on a person and can send back to the computerized monitoring system the 3D coordinates of the joints in the person's body and a skeletal outline of the person. As a non-limiting example, a person's right arm can be at time TI located at coordinates (x1, y1, z1) in a picture frame taken by the camera. At time T2 the right arm is captured by the picture frame taken by the camera at coordinates (x2, y2, z2). Based on this information, motion, speed and direction can be derived utilizing the elapsed time and comparing the two 3D coordinates over the elapsed time. The camera preferably views the entire bed or a large portion of the bed or other area that the patient is resting at (i.e. chair, couch, etc.) simply by its placement in a manner sufficient for the monitored area to be visible to the camera. Thus, the camera does not require any triggering event to cause the camera to begin recording video and/or 3D depth data or transmitting video and/or 3D depth data to the other components of the system for analysis. As the video camera is recording or otherwise transmitting video and/or 3D depth data to the other system components at all times during monitoring, the electronic device is able to immediately track, capture and/or record the |

| | |
|---|---|
| | monitored individual's movements at all times within the room or monitored area and will be able to provide information as to whether and when the individual begins to move or begins to get up to move. Preferably the 3D Camera, Motion and Sound Sensor records, captures and/or streams video and/or 3D depth data. As video is technically made up of individual picture frames (i.e. 30 frames per second of video), the above reference to picture frames is referring to frames of video.<br>Depth sensitivity can come into play with skeletal tracking in order to minimize false alarms, as objects behind and in front of the patient can be effectively ignored. The preferred use of depth as a factor also differentiates the current monitoring system from motion/object detection systems that rely on 2D images.<br>The 3D Motion and Sound Sensor is located within the room of the patient being monitored and potentially just outside of the patient's room. It is connected to the computerized communication and computerized monitoring systems via a data connection (TCP/IP or comparable technology). |
| Computerized Virtual Safety Rail Monitoring System | A computer system specifically designed and programmed to create virtual safety rails around a specific object such as a hospital bed and which monitors activity based on information received from the 3D Camera, Motion and Sound sensor(s). The computerized monitoring system will preferably be located within the patient's room and can be connected to the centralized monitoring station at the facility but can also be located at any physical location so long as a data connection (TCP/IP or comparable technology) exists between the computerized monitoring system, the computerized communication system, centralized monitoring station and/or 3D motion and sound sensor. The computerized virtual safety rail monitoring system preferably makes its determinations based on the data received by the 3D Camera, Motion and Sound sensor(s). |
| Computerized Communication System | A computer system specifically designed and programmed to facilitate communication between the monitored patient and computerized monitoring system in the event the virtual safety rails are crossed. This system may include but is not limited to amplified speakers, microphones, lights, monitors, computer terminals, mobile phones and/or other technologies to allow for the electronic communication to take place. The computerized communication system will preferably be located within the patient's room being monitored but certain components of the system are mobile by their nature (i.e. mobile phones, pagers, computers) and can also be located at any location so long as a data connection (TCP/IP or comparable technology) exists between the computerized monitoring system, the computerized communication system, centralized monitoring station and 3D Camera, Motion and Sound sensor. |
| System Database | A computer database that stores records of all alerts generated, notifications, confirmation requests, responses, and reconfirmation requests and any other desired information concerning a triggering event or lack of triggering event(s). |
| Centralized Monitoring Primary Display | A computer display connected to the centralized monitoring station, showing video and audio of all patient rooms connected to the centralized monitoring station. |
| Centralized Monitoring Alert Display | A computer display connected to the centralized monitoring station, showing video and audio of any patient room where an individual is deemed to have crossed a virtual safety rail at the moment such determination is made. |
| Caregiver | A relative, friend, individual, company or facility whose purpose is to provide assistance in daily living activities for individuals who are disabled, elderly or otherwise in need of assistance. |

DETAILED DESCRIPTION OF THE INVENTION

Figure 1:
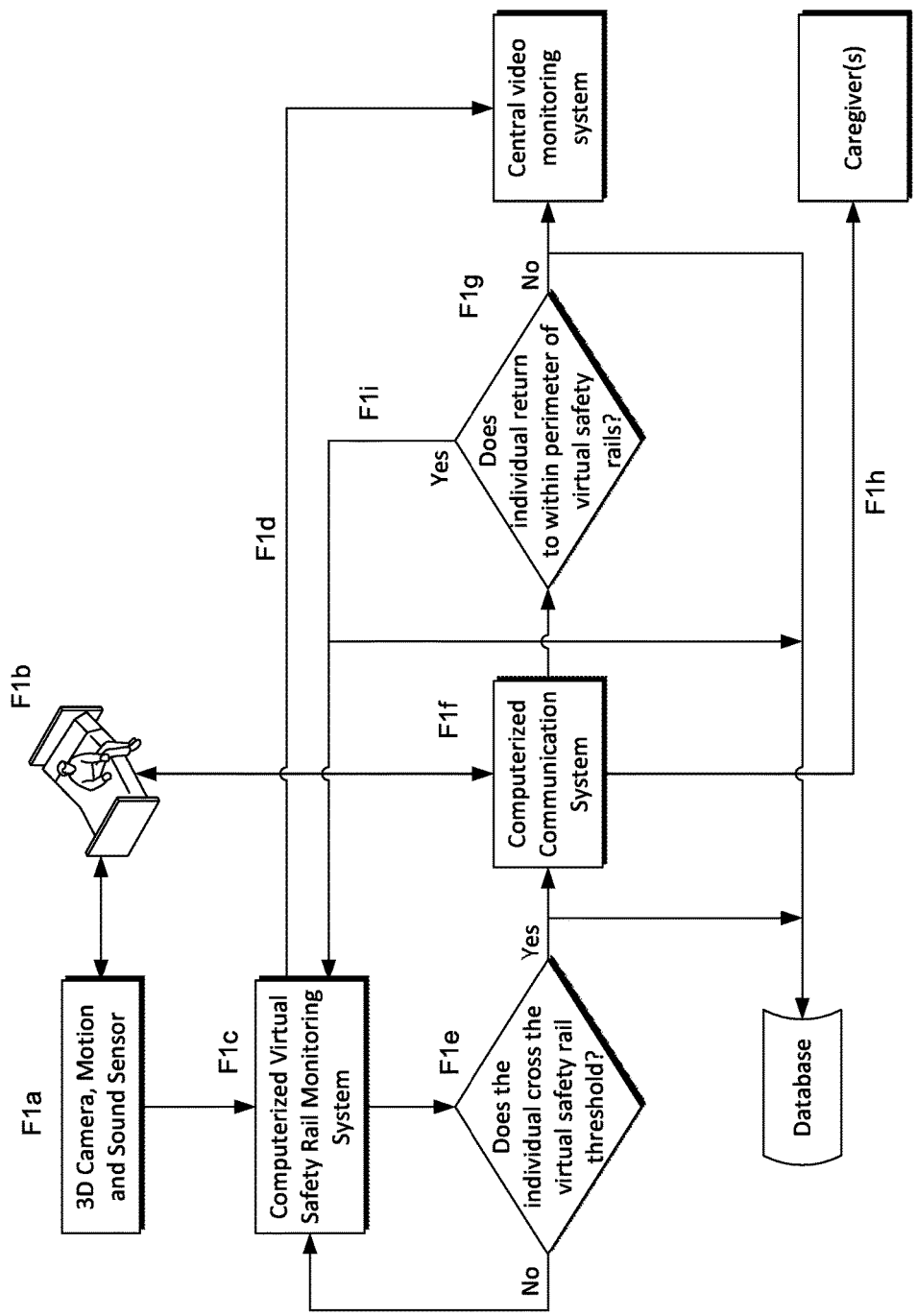
FIG. 1 is a block diagram of a virtual safety rails configuration, monitoring and alerting system and method in accordance with the present invention.

FIG. 1 illustrates a block diagram for the virtual safety rails configuration, monitoring and alerting system and method of the present invention. Specifically, FIG. 1 shows the workflow for monitoring an individual's status through the use of one or more 3D Camera, Motion and Sound sensors.

At step F1a, one or more 3D Camera, Motion and/or Sound sensors can be installed in the patient's or individual's room. At step F1b, the one or more 3D Motion and Sound sensors can be configured to recognize the individual using biometric identifiers such as height, distance between points on the body, etc. Virtual safety rails can also be calibrated at this time. At step F1c, data from the 3D Motion and Sound sensors can be sent to a Computerized Virtual Safety Rail Monitoring System. At step F1d, a continuous video feed can be sent to the central Video Monitoring System.

At step F1e, if the computerized virtual safety rail monitoring system detects that the patient or any part of the patient has crossed outside of the designated perimeter (beyond the virtual safety rail), the monitoring system will alert the computerized communication system. A record can also be entered in a database to record the incident. If other individuals such as a caregiver are also detected at the time the virtual safety rail threshold is crossed, the system can be designed or programmed such that no alert is generated and it will continue to monitor the data being sent from the 3D camera, motion and sound sensor. Additionally, the system can be programmed to be capable of detecting pre-programmed hand, arm, leg and body gestures from the patient individual and/or another person in the room to initiate an alert to the computerized communication system. As a non-limiting example, a particular hand gesture could be used as a signal to send medical assistance or that the individual needs to use the restroom. Further examples are numerous.

At step F1f, the computerized communication system preferably can first issue a verbal warning to the patient that they have crossed the virtual safety rail threshold. This verbal warning can be a pre-recorded message, including, but not limited to, a pre-recorded message from an caregiver, and will advise the patient to return to within the perimeter of the virtual safety rails. At step F1g, should the patient fail to return to within the perimeter of the virtual safety rails in a timely manner, an alert can be generated on the central Video Monitoring System (see FIG. 2). The system database can also be updated to reflect actions taken. The system can be designed to provide visual and/or audio alerts.

At step F1h, the computerized communication system can notify caregivers or other designated persons that the individual requires assistance. Notification of caregivers can be made through phone call, text messaging, speakerphone systems, pagers, email, or other electronic means of communication if so desired and configured. At step F1i, if the individual returns within the perimeter of the virtual safety rails, the system database can be updated to reflect such. Additionally, the system will continue to monitor the patient and store all data in the system database.

Preferably, based on information received from the sensor(s), the computerized monitoring system can track skeletal points on a body of the specific individual being monitored in real time. The 3D Camera, Motion and Sound sensors continually capture data concerning the one or more rooms regardless of whether (and independent of) any movements or sounds have occurred in the one or more rooms. Thus, during monitoring, the 3D Camera, Motion and Sound sensors continually capture or receive data at all times and continually feed or send the data to the computerized monitoring system for processing and analysis involved in making the relevant determinations.

The monitored individual or a person/caregiver with the monitored individual can receive a message from the computerized communication system which is in communication with the computerized monitoring system to determine whether or not the individual needs assistance. In one embodiment, the computerized monitoring system detects or determines that the individual may have fallen or is about to fall or crossed over a virtual safety rail, solely from the video feed forwarded from the one or more 3D Camera, Motion and Sound sensors that shows that the individual has fallen or gestured that he or she needs assistance or moved over or through the electronically defined virtual safety rail.

Figure 2:
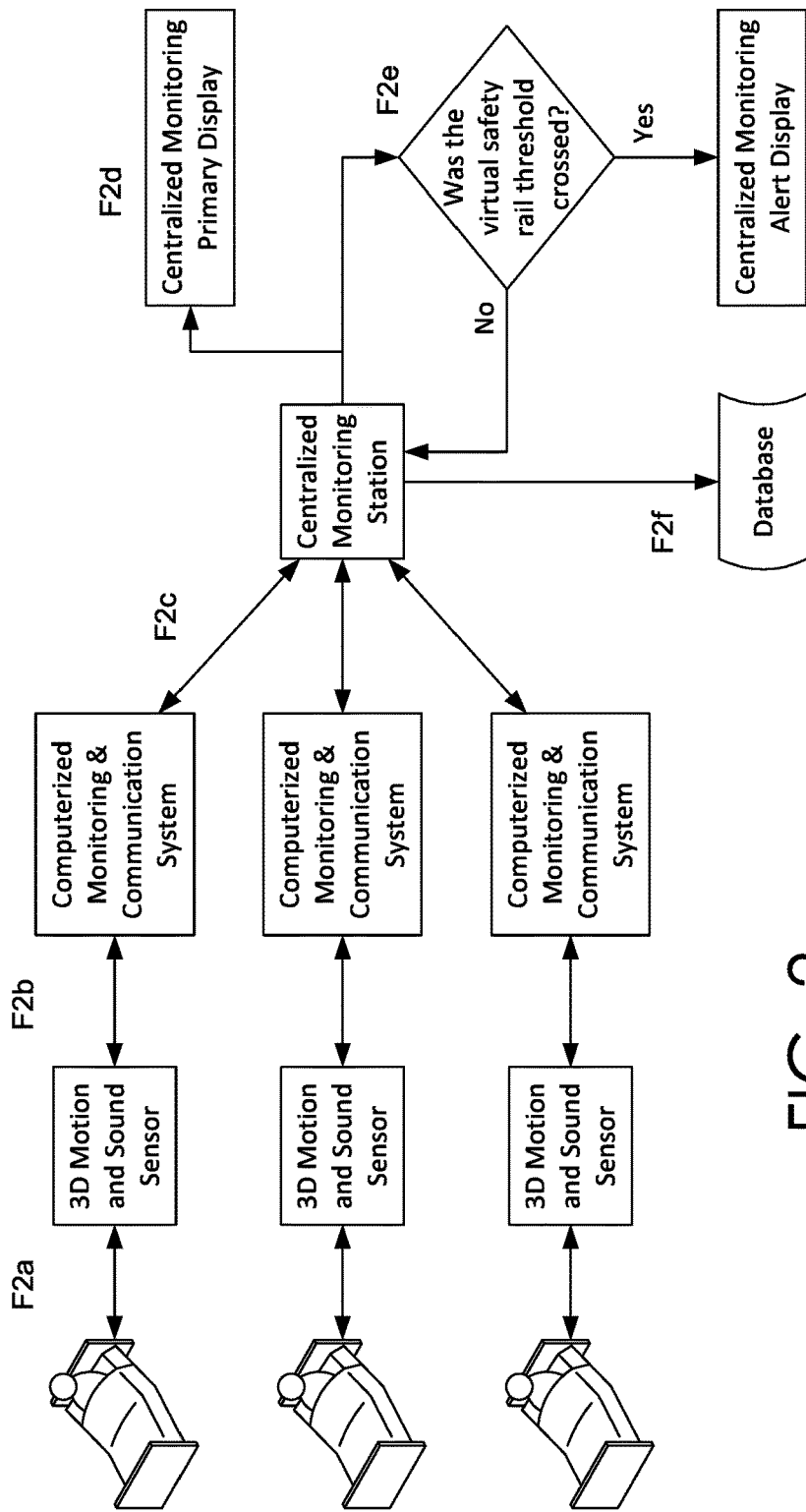
FIG. 2 is a block diagram of a centralized monitoring and alerting system in accordance with the disclosure.

FIG. 2 illustrates a block diagram for centralized monitoring and alerting and shows the workflow for centralized monitoring and alerting of the central monitoring regarding whether an individual has crossed a virtual safety rail threshold through the use of 3D Motion and Sound sensors. At step F2a, one or more 3D Motion and Sound sensors are installed in and/or just outside an individual's room, home, hospital room, or other place of temporary or permanent residence and are connected to the computerized monitoring and communication systems as described in FIG. 1. The video, audio and alert data can be sent to a centralized monitoring station where the data is aggregated. Preferably, the centralized monitoring station receives data at all times from the sensors to allow the various individuals to be constantly monitored at the centralized station regardless of whether or not a fall has been detected.

At step F2b, all video, audio and alert feeds received by the centralized monitoring station can be displayed on the centralized monitoring primary display. Alternatively, multiple centralized monitoring primary displays can be utilized based on the quantity of rooms to be monitored at a given time. At step F2c, when the centralized monitoring system receives an alert from any of the computerized monitoring and communication systems indicating that an individual in any of the monitored rooms or other locations has fallen, the video, audio and alert information is displayed on the Centralized Monitoring Alert Display. Should the centralized monitoring station receive alerts from more than one of the computerized monitoring and communication systems indicating that an individual in a monitored room or location has crossed a virtual safety rail threshold, the centralized monitoring alert display will display the video, audio and alerting information from all such instances at the same time. If no alert is received by the centralized monitoring station, nothing is displayed on the Centralized Monitoring Alert Display. At step F2d, an electronic record of any alerts received by the Centralized Monitoring Station can be stored in an electronic database, which is in communication with the Centralized Monitoring Station.

Figure 3:
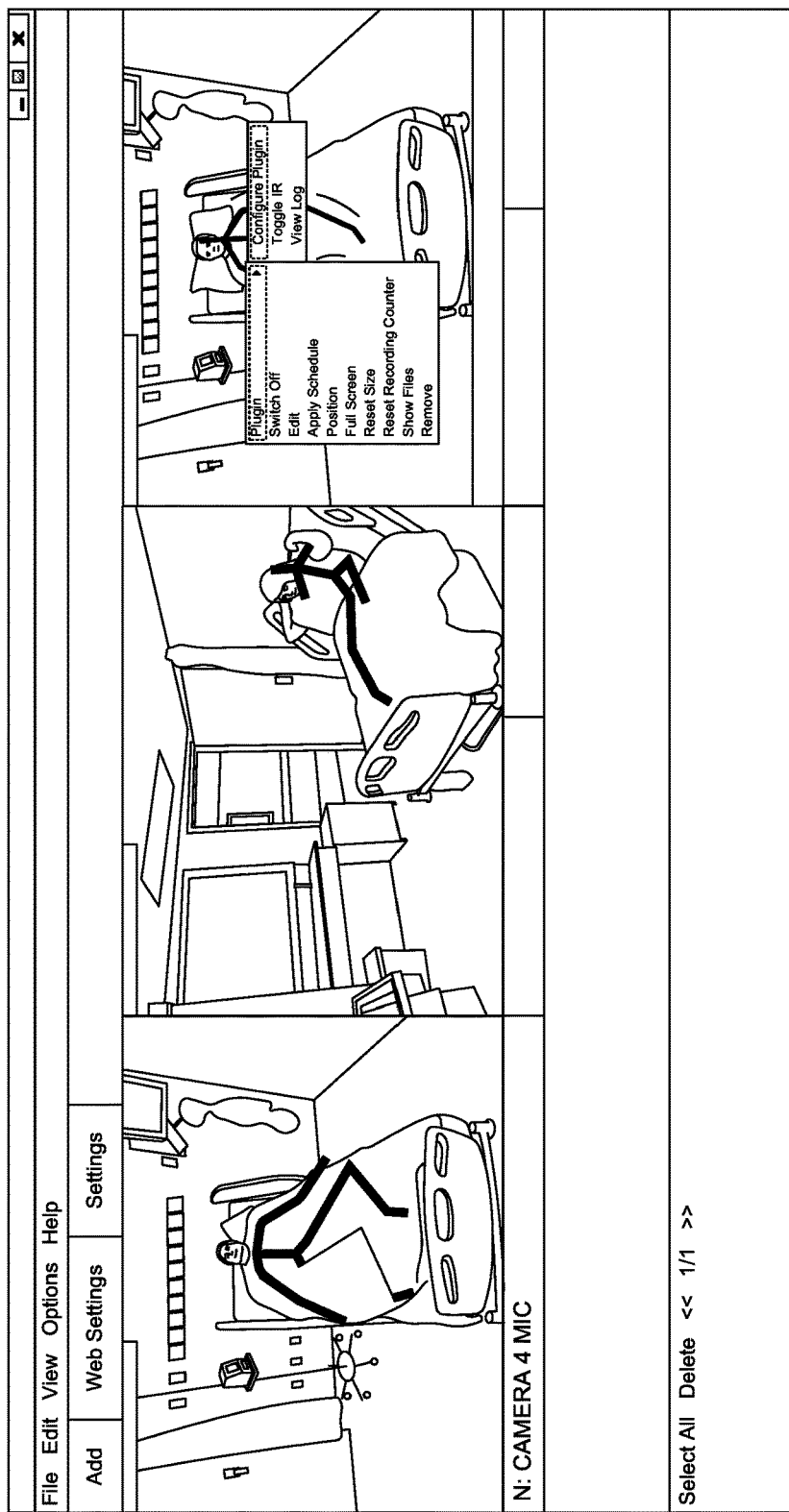
FIGS. 3 though 15 illustrate various screen shots for configuring the system for operation including defining bed zone, virtual safety rails and alert types.

FIGS. 3 through 15 illustrate several set up screen shots for configuring the bed zone, virtual safety rails and alert types. In FIG. 3, the bed zone and virtual safety rails can be configured for a given or specific 3D Motion and Sound Sensor. To begin configuration, the user can hover over the 3D Motion and Sound Sensor video window with the cursor, right-click, select plugin and then select configure plug-in. A window will popup showing the 3D Motion and Sound Sensors' feed. The user selects the icon for the type of zone or rail they wish to draw, which as a non-limiting example and for illustrative purposes, can be a bed zone and virtual safety rail(s) (See FIG. 4).

Figures 4, 5:
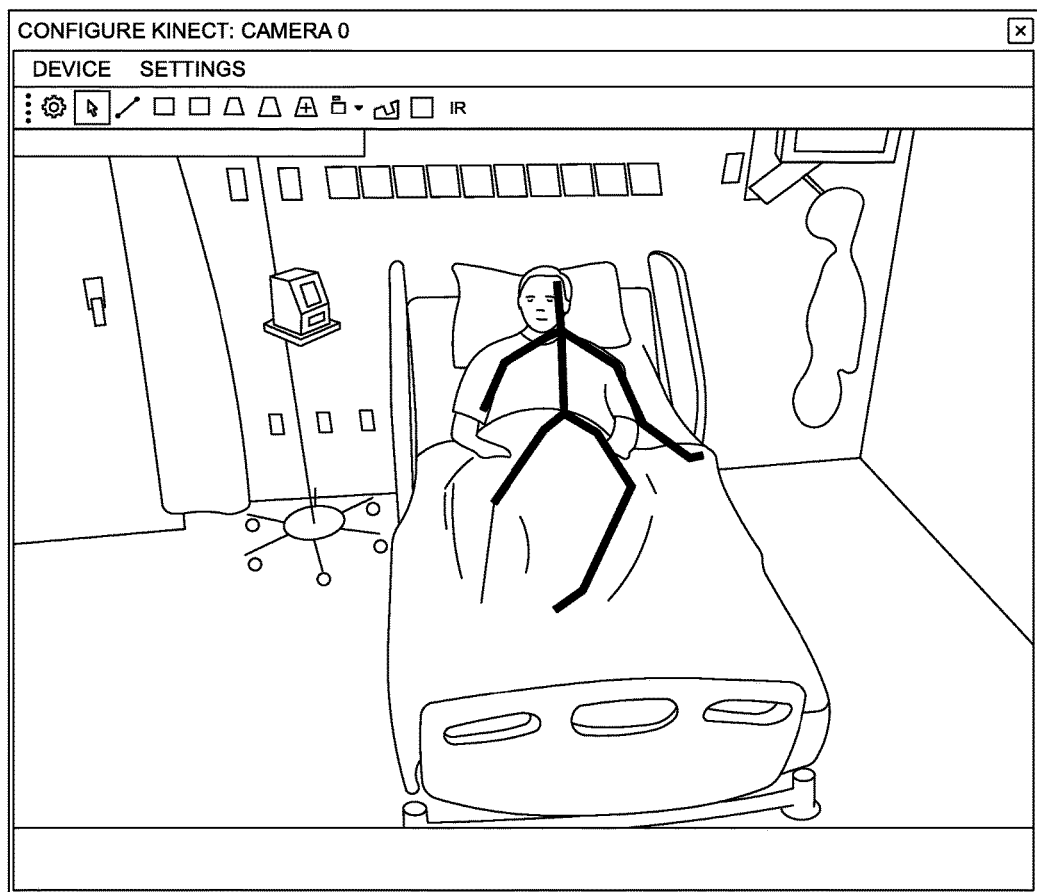

As non-limiting examples, the icons that appear on the screen for selection can include the following symbols shown in FIG. 5. In this non-limiting example, in no particular order, some of the icons include Bed Zone, Auto Bed Zone (Select Patient), Auto Bed Zone (Auto-select), Saved Zones, Virtual Safety Rail and Clear All.

Figure 6:
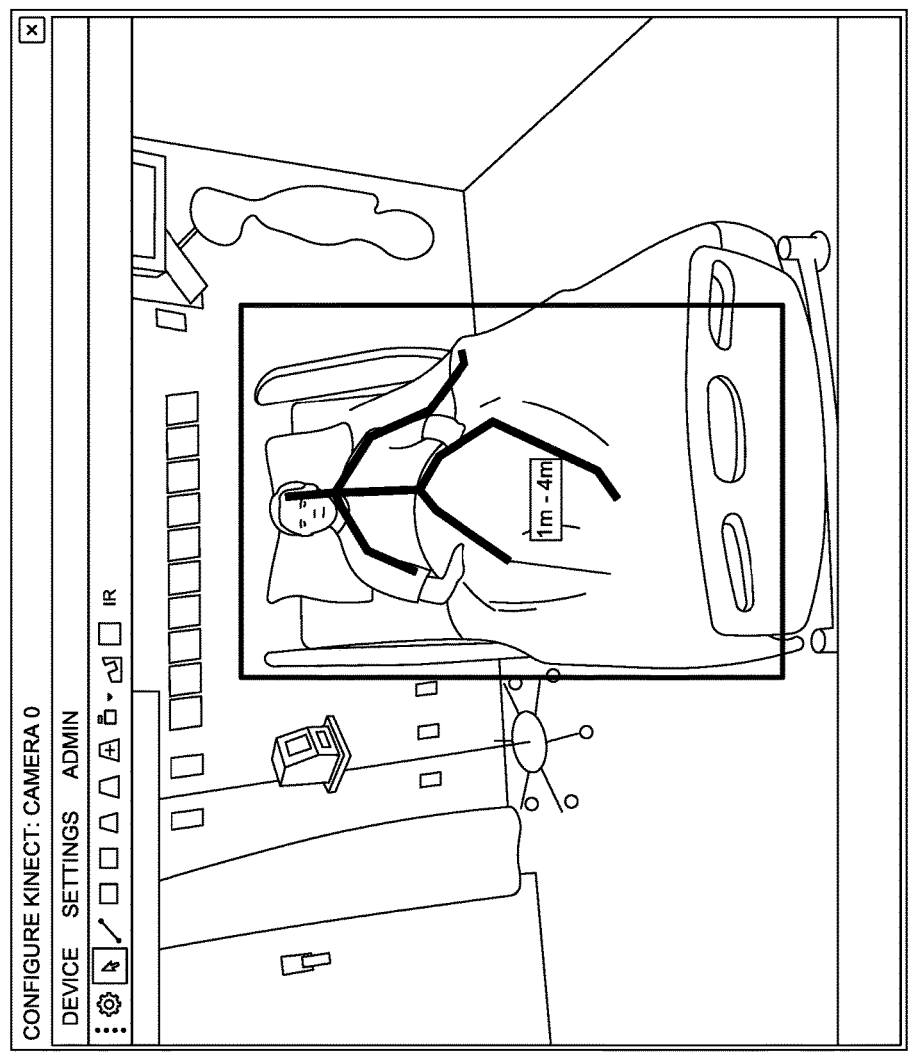
Figure 8:
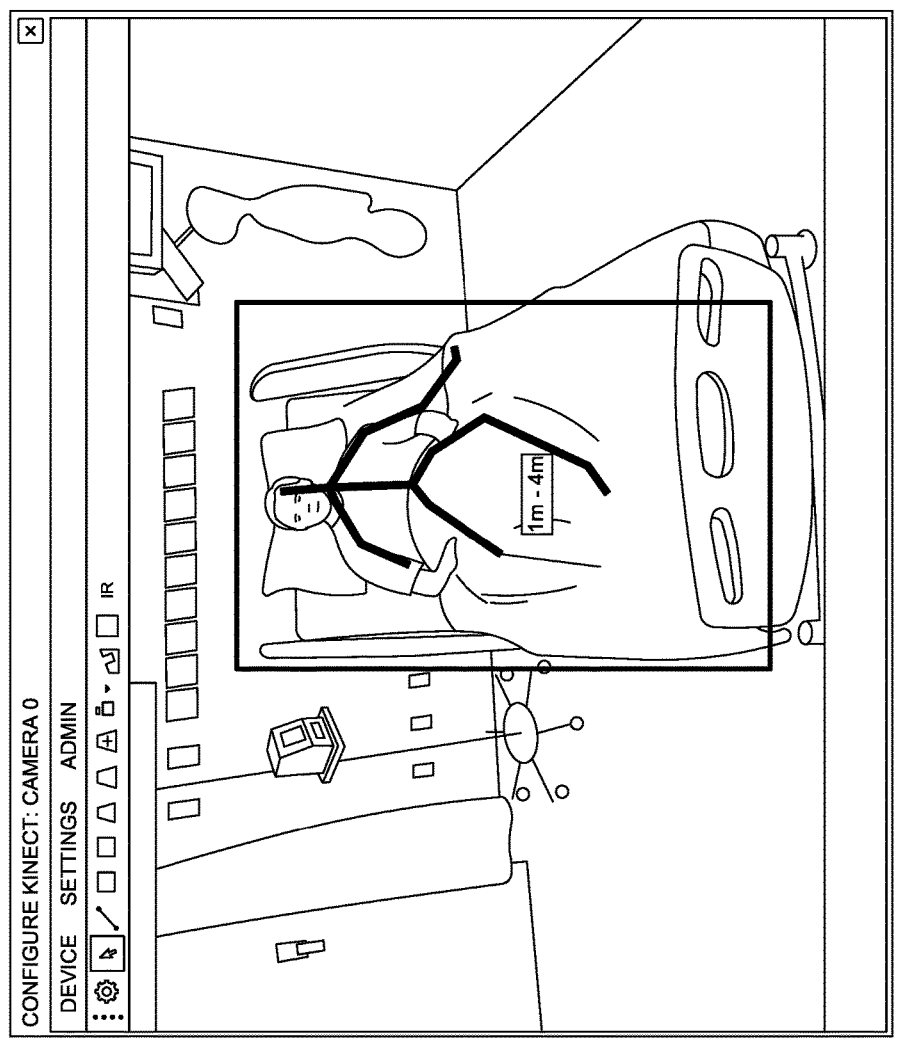

As seen in FIG. 6, to place a zone, the user clicks on the screen where he or she would like to start the zone. Then, the cursor is moved to the corner point for the zone and clicked again. The user continues to select additional points until the zone is drawn to the user's satisfaction. Preferably, the user clicks on the round end point of the beginning of the zone to complete the zone (See FIG. 6). When the zone has been completed, the zone can appear and a depth range box (i.e. square, rectangle, etc. disposed over the patient on the screen) can be provided on the screen, such as, but not limited to, in the middle of the screen or zone (see FIG. 8), though any location on the screen is considered within the scope of the invention. Placing a virtual rail is done with a similar process wherein the user clicks on the screen where he or she would like to start the rail. Then the cursor is moved to the end point for the rail and the user clicks on the screen again to place the rail. As seen in FIG. 8, upon completion, the zone and/or rail(s) appear and has a depth range box preferably in the middle.

Figure 7:
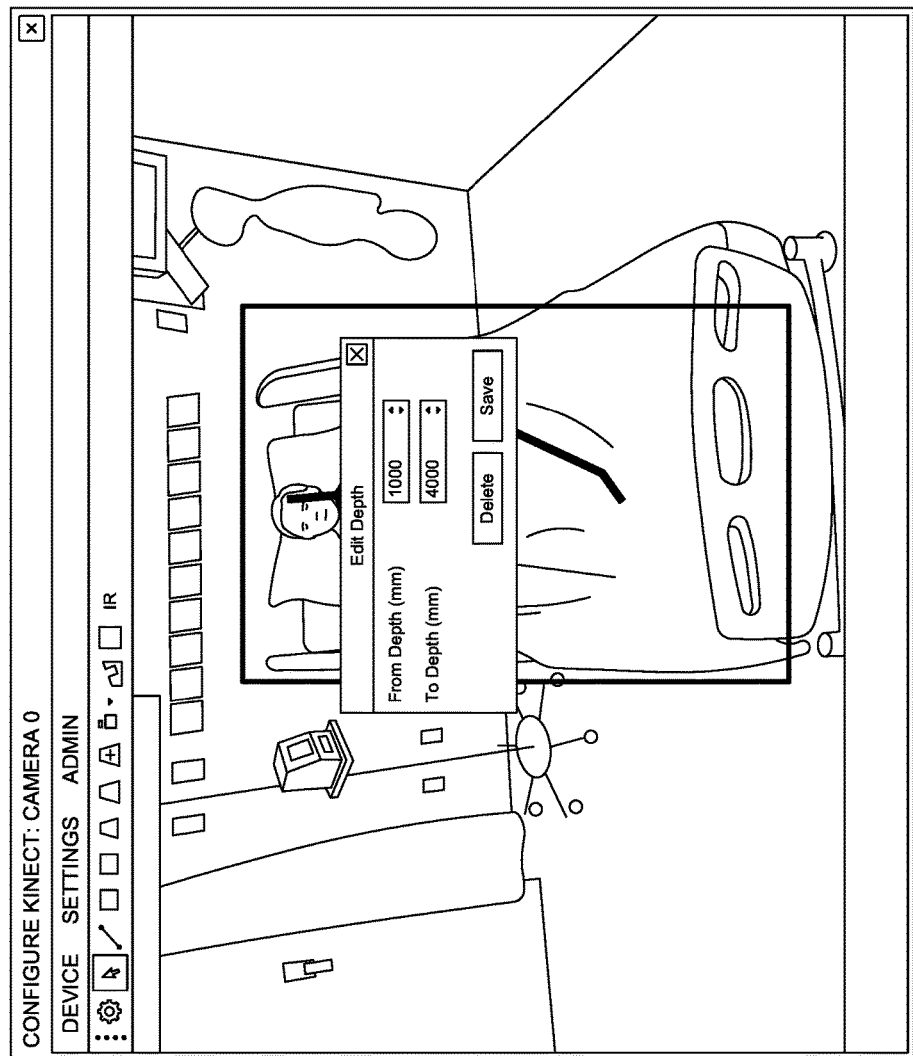

As seen in FIG. 7, the user can adjust the depth range for any given zone or rail. By preferably double clicking on the depth range box or by other conventional selection methods, an Edit Depth window can appear. The user can enter in the depth ranges (preferably in millimeters (mm) though not considered limiting) and then the user can click the Save button or icon when done to store the entered values.

If there are any other types of zones or rails to draw for the particular sensor, the above steps are repeated to place the next zone or rail and the depth setting can be adjusted for each if necessary. Additionally, all zones and rails can be cleared by clicking on or otherwise selecting the Clear All icon in the toolbar. Once all of the zones/rails are configured, the user can close the window to finish or the user has the option to save the zone rail configuration for later use.

Figure 9:
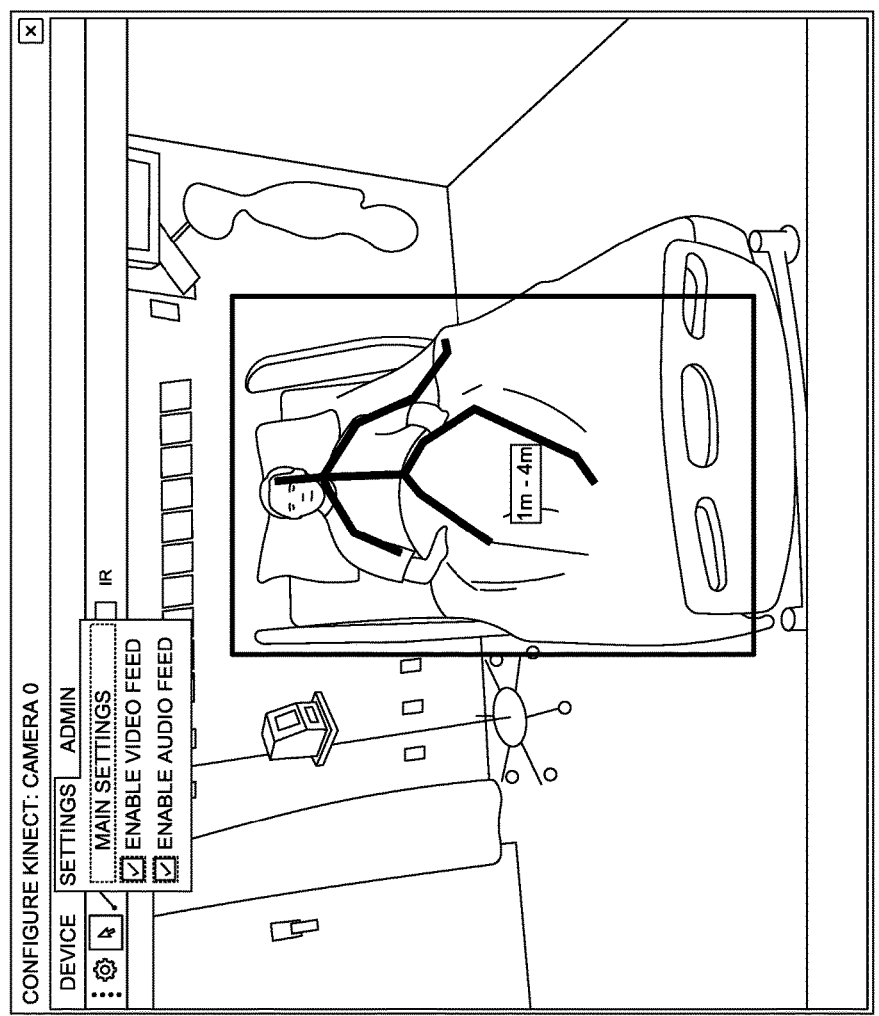

As seen in FIG. 9, to access the main settings window, the user can click or otherwise select the Settings menu and the select Main Settings from the drop-down list. As one non-limiting alternative, the user can click on the Gear icon (⚙) or other designated icon in the toolbar to access the main settings window.

Figure 10:
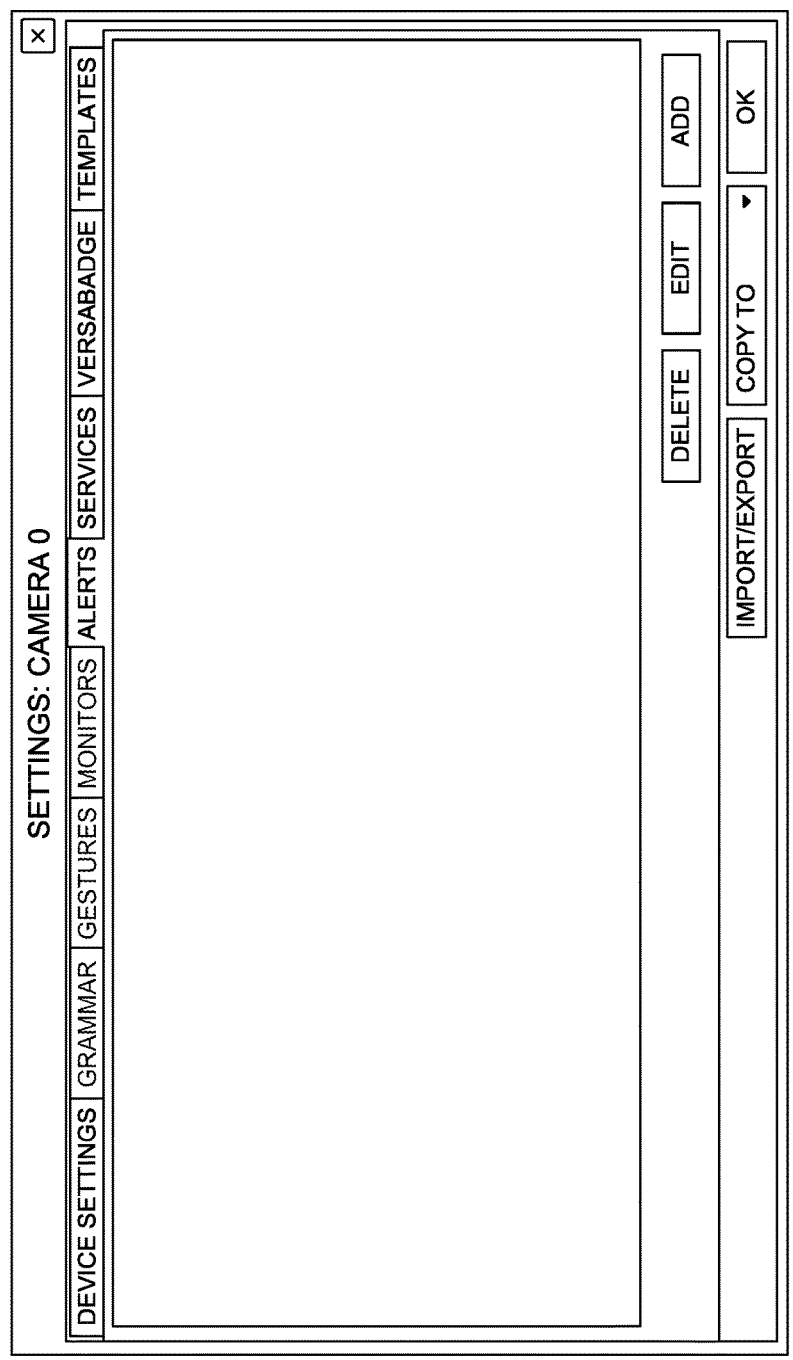
Figure 11:
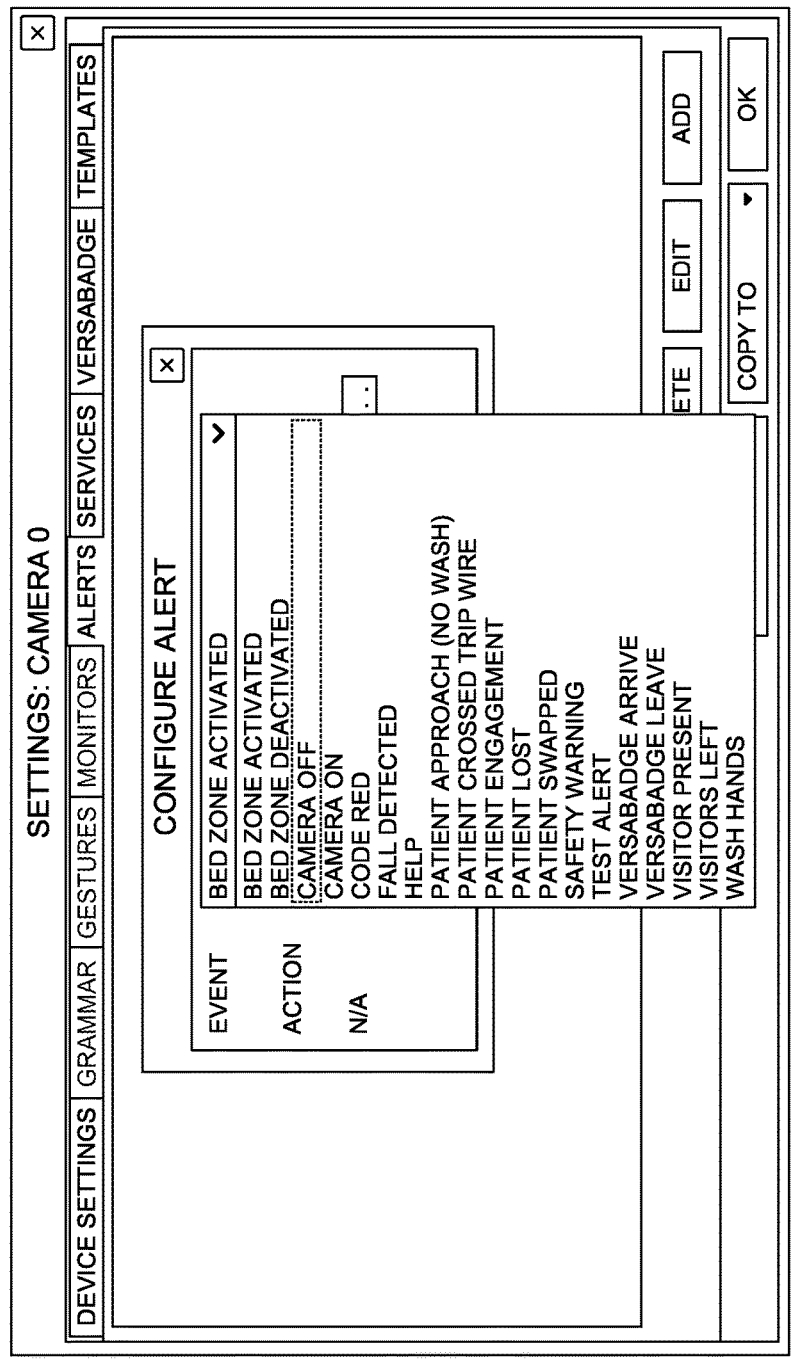

As seen in FIG. 10, for one non-limiting way to configure a new Alert, the user can select the Alerts tabs and then click on or otherwise select the Add button, which can result in the Configure Alert box appearing on the screen (See FIG. 11). As seen in FIG. 11, under the Event field, the user can then select the event from the drop down list that the user wishes to send an alert on.

Figure 12:
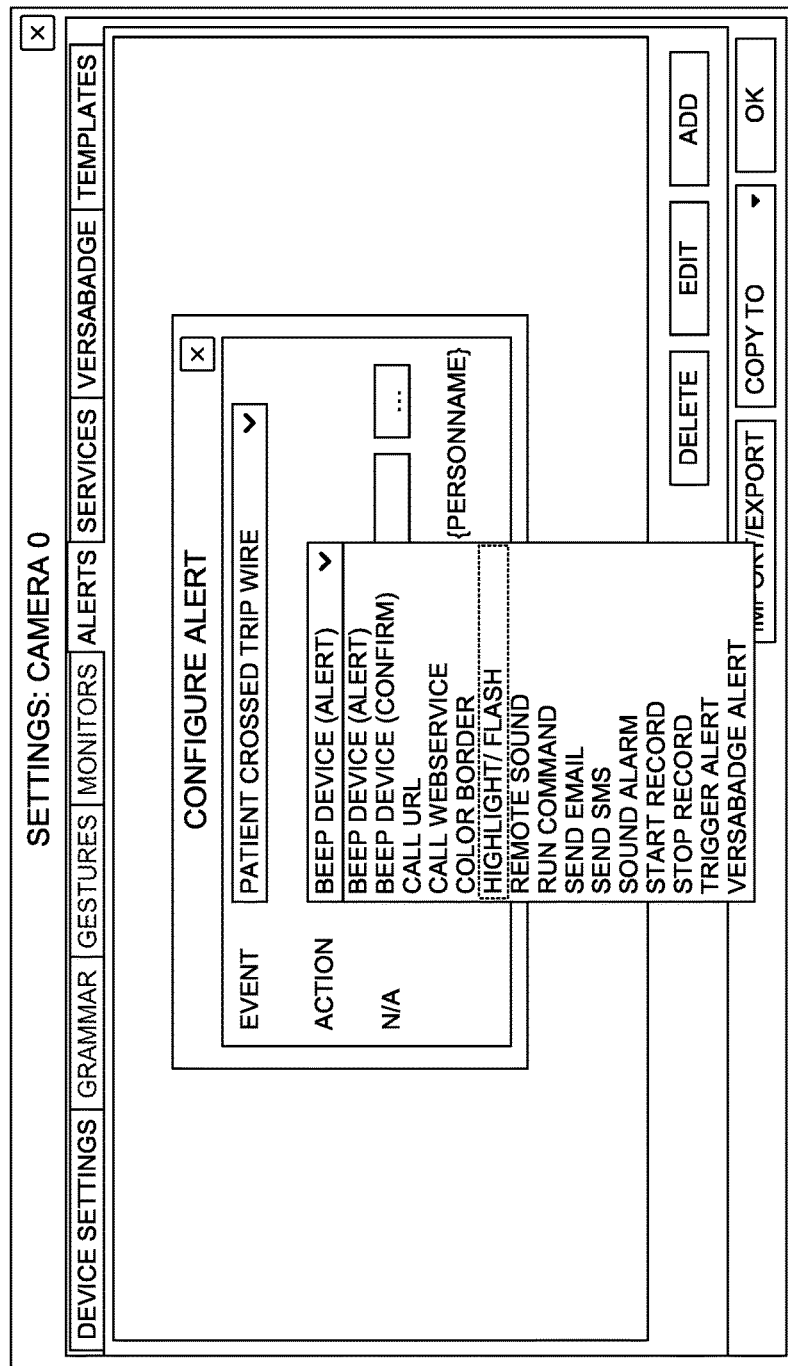
Figure 13:
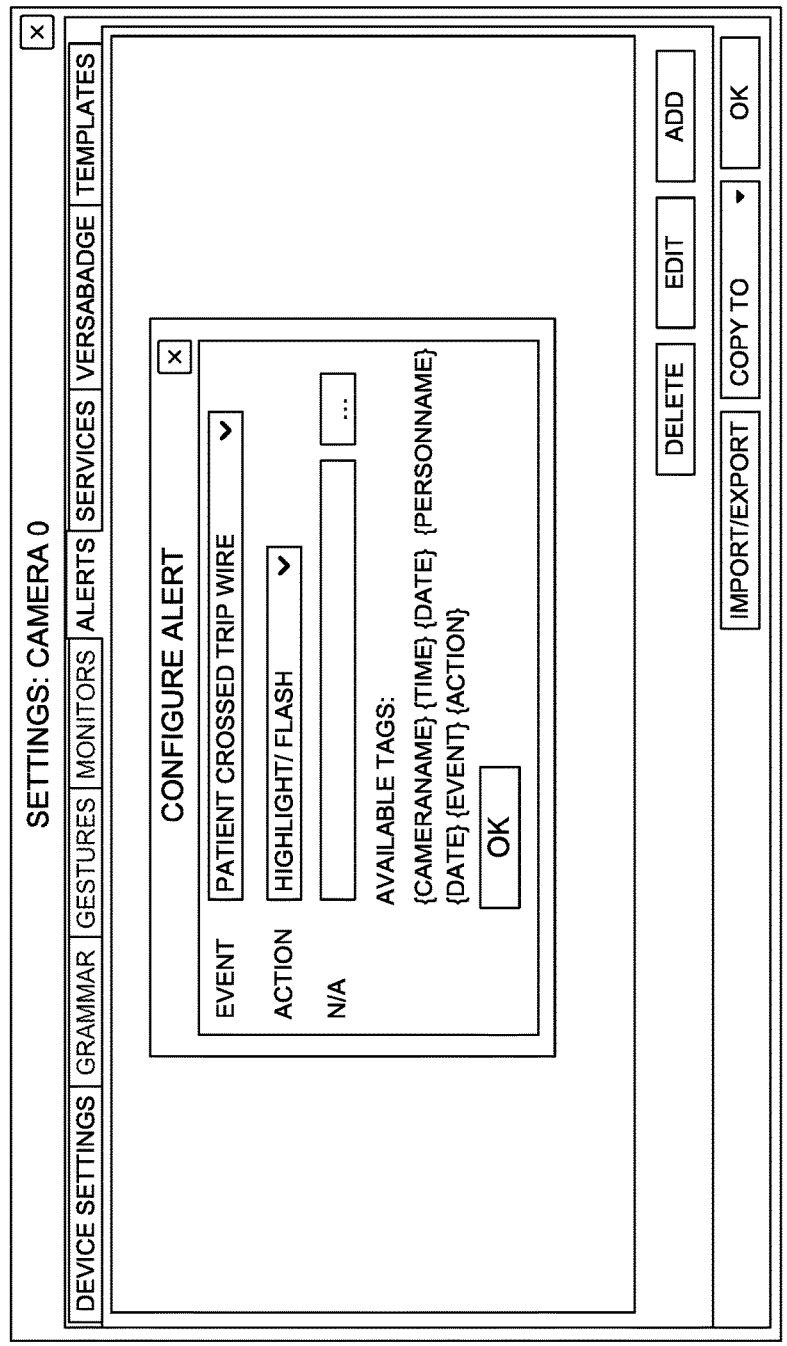
Figure 14:
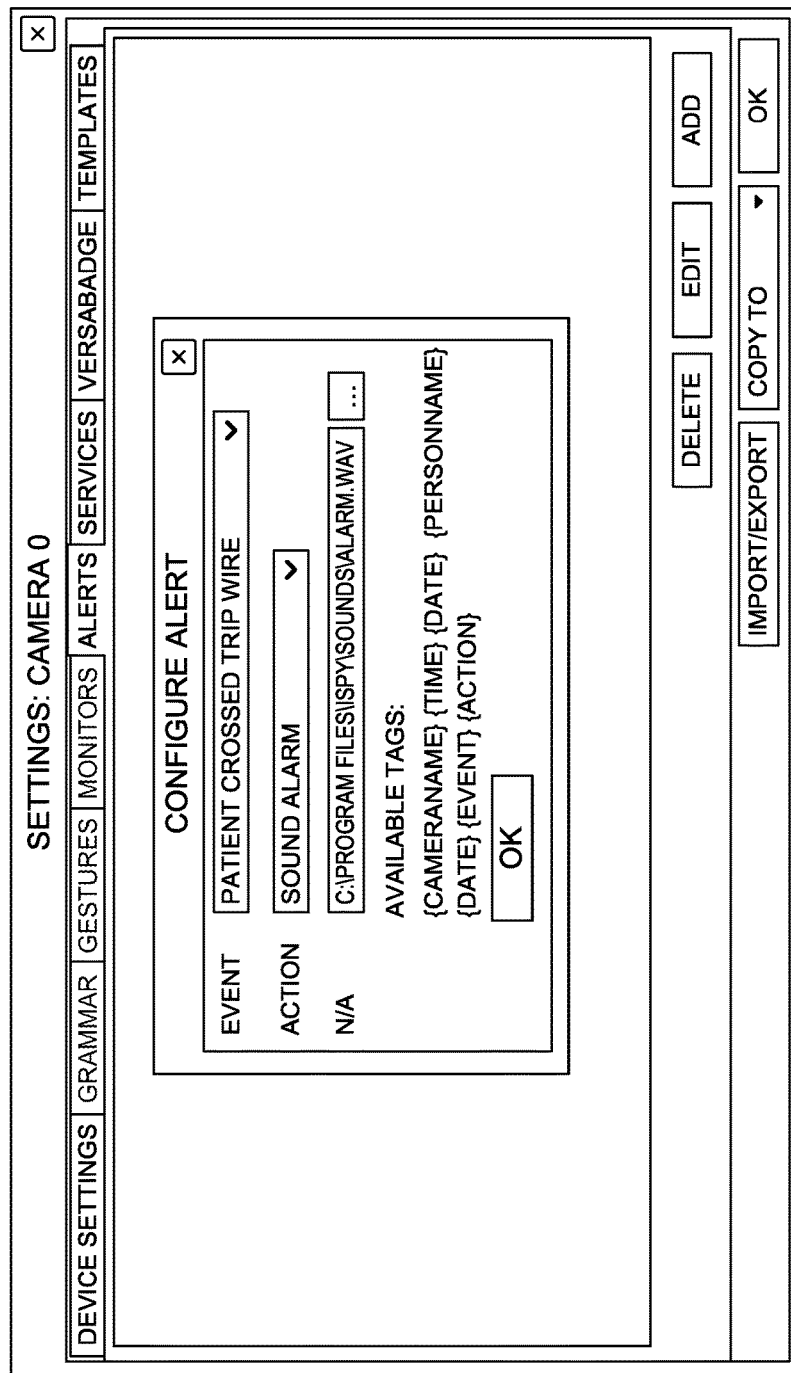
Figure 15:
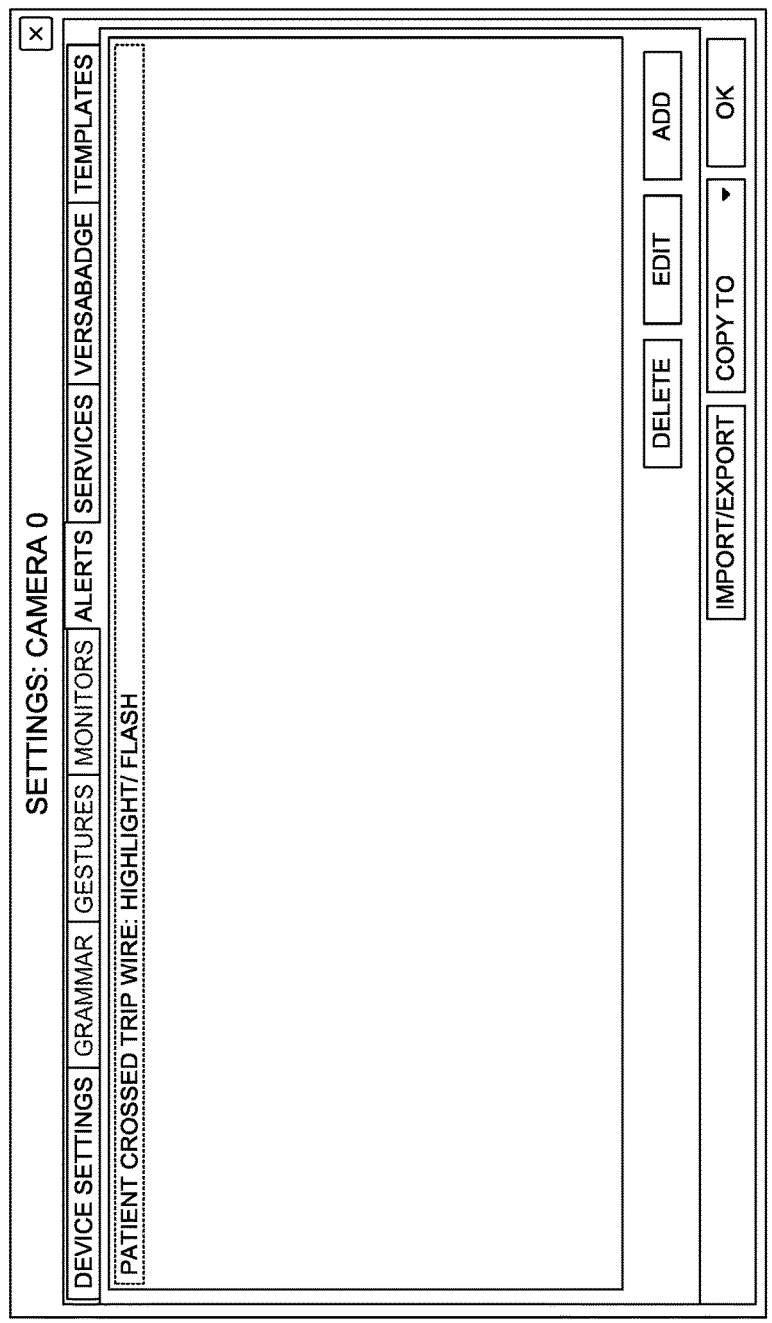

As seen in FIG. 12, once the Event type is selected, under the Action field, the user can select the Action he or she wishes to have the system perform when the selected Event is detected. Once the Event and Action have be selected, the OK button (See FIG. 13) can be selected to save the selected entries.

For certain Actions, an additional field may need to be completed to finish the Action. If the field is required, it can appear below the Action dropdown (See FIG. 14), If no further fields are required, the Configure Alert box can display N/A (See FIG. 13) or just be blank. As mentioned above, once all settings are selected, the user clicks or otherwise selects the OK button, which causes the new Alert to be listed in the Alerts tab window. To edit an existing Alert, the user first clicks on or otherwise selects the Alert and then selects the Edit button (See FIG. 15). To delete an Alert, the user can first highlight it and then click on the Delete button (See FIG. 15).

To add more Alerts, the user clicks or selects the Add button and repeats the above described steps. Once finished, the user clicks on or otherwise selects the bottom corner OK button to save and close the window.

Figure 16:
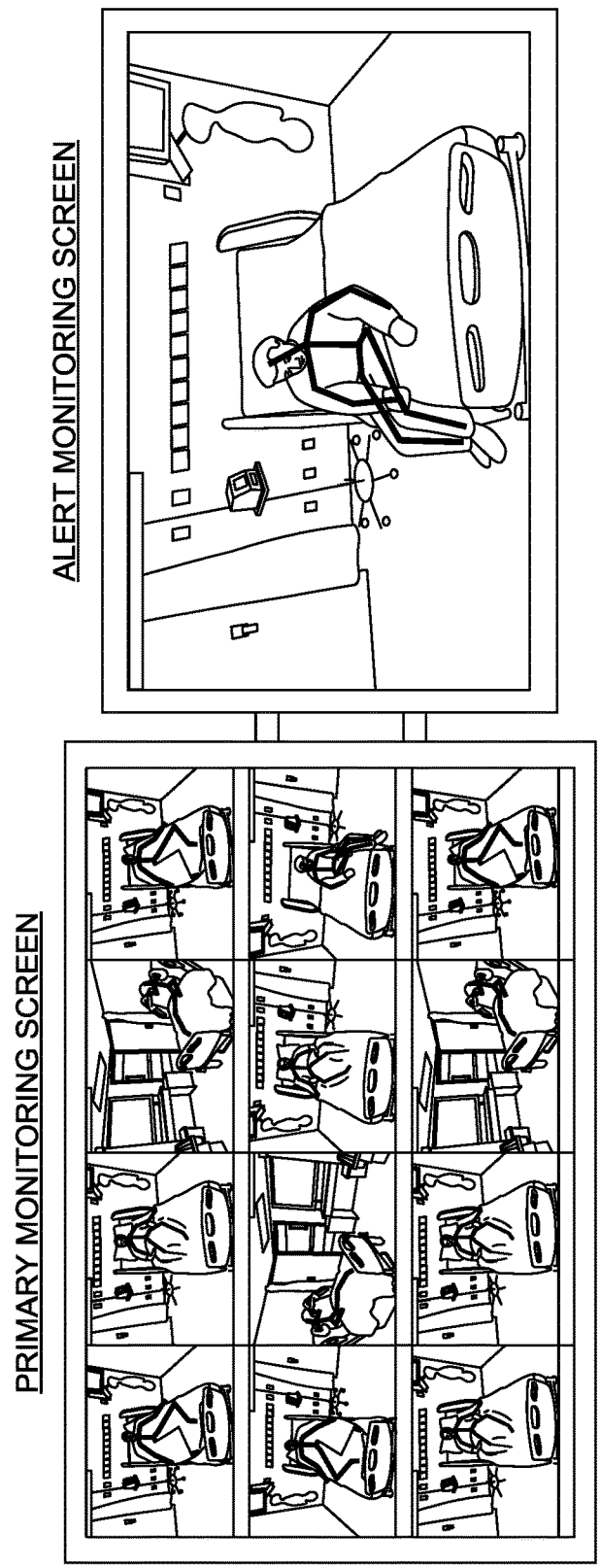
FIG. 16 is a non-limiting example of a centralized video monitoring system that can be used with the system and method shown in FIG. 1.

FIG. 16 shows a non-limiting example of a centralized video monitoring system that can be used with the system and method. The window highlighted in red is a non-limiting example of an alert that can be generated when the patient fails to return to within the perimeter of the virtual safety rails.

The above described system uses several components, including, but not limited to:
1. One or more 3D Camera, Motion and/or Sound Sensors. However, it also within the scope of the invention to eliminate the sound sensor and have the functions of the invention be performed with only motion/camera functions;
2. A Computerized Virtual Safety Rail Monitoring System in electronic communication with the one or more 3D Camera, Motion and Sound sensors;
3. A Computerized Communication System in electronic communication with the Computerized Virtual Safety Rail Monitoring System;
4. A Centralized Monitoring Station in electronic communication with the one or more 3D Camera, Motion and Sound sensors, Computerized Virtual Safety Rail Monitoring System and/or Computerized Communication System;
5 A Centralized Monitoring Primary Display in electronic communication with one or more Centralized Monitoring Stations;
6. A Centralized Monitoring Alert Display in electronic communication with one or more Centralized Monitoring Stations; and/or
7. Database The various components can be in electrical, wired and/or wireless communication with each other.

The automatic detection of an individual leaving a prescribed virtual perimeter will provide significant administrative and clinical benefits to caregivers and individuals alike, including the following non-limiting public benefits:
1. Automation of determination of perimeter violation and automated notification of caregivers or other designated entities.
2. Ability to alert patients and caregivers in time to prevent patients from getting out of bed.
3. Reduction in response time for individuals who have fallen and require assistance.
4. Increased survival rate for individuals who have experienced a fall.
5. Reduction in costs for hospitalization and medical care related to complications from a fall.
6. Ability to distinguish multiple individuals and prevent false positives.
7. Ability to distinguish direction of motion to prevent false positives.
8. Ability to provide a video feed of a patient under all lighting conditions to the central video monitoring system.
9. Audio and gesture based recognition to allow multiple forms of communication with patient.

Any computer/server/electronic database system (collectively "Computer System") capable of being programmed with the specific steps of the present invention can be used and is considered within the scope of the disclosure. Once programmed such Computer System can preferably be considered a special purpose computer limited to the use of two or more of the above particularly described combination of steps (programmed instructions) performing two or more of the above particularly described combination of functions.

All components of the described system and their locations, electronic communication methods between the system components, electronic storage mechanisms, electronic notification technologies, etc. discussed above or shown in the drawings, if any, are merely by way of example and are not considered limiting and other component(s) and their locations, electronic communication methods, electronic storage mechanisms, electronic notification technologies, etc. can be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts described in the specification that are related to the function of the "means for" language.

While the system and method have been described and disclosed in certain terms and as disclosed certain embodiments or modifications, persons skilled in the art who have acquainted themselves with the disclosure will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A system for detecting when a monitored individual or any part of the monitored individual has crossed outside of a designated electronic perimeter, the system comprising:
   one or more 3D camera, motion and sound sensors within a room occupied by a specific individual to be monitored, the one or more 3D camera, motion and sound sensors configured to:
      recognize one or more biometric identifiers of the specific individual; and
      electronically forward a continuous video feed to a computerized virtual safety rail monitoring system;
   wherein the computerized virtual safety rail monitoring system is configured to:
      electronically designate virtual safety rails defining a designated electronic perimeter within an area of the room; and
      detect whether the specific individual or any part of the specific individual has crossed over the designated electronic perimeter based on 3D information from the continuous video feed received from the one or more 3D camera, motion and sound sensors; and
   a centralized monitoring station configured to receive and display the continuous video feed.

2. The system of claim 1, wherein, upon detecting that the specific individual or any part of the specific individual has crossed over the designated electronic perimeter, the computerized virtual safety rail monitoring system is configured to send an electronic alert to a computerized communication system.

3. The system of claim 1, wherein upon detecting that the specific individual or any part of the specific individual has crossed over the designated electronic perimeter, the computerized virtual safety rail monitoring system is configured to send an electronic alert to a computerized communication system if the specific individual is alone, and the electronic alert is not sent if another individual is also detected at a time the designated electronic perimeter is crossed.

4. The system of claim 1, wherein the 3D camera, motion and sound sensors are configured to continue sending the video feed to the computerized virtual safety rail monitoring system after it is detected that the specific individual or a part of the specific individual has crossed outside of the designated electronic perimeter.

5. The system of claim 2, wherein the centralized monitoring station receives the continuous video feed from the computerized virtual safety rail monitoring system.

6. The system of claim 5, wherein the centralized monitoring station aggregates continuous video feeds for multiple individuals to be monitored.

7. The system of claim 6, wherein the centralized monitoring station comprises a primary monitoring display.

8. The system of claim 7, wherein the centralized monitoring station displays the video feeds for each of the multiple individuals to be monitored on the primary monitoring display.

9. The system of claim 7, wherein the centralized monitoring station is configured to receive an alert from the computerized virtual safety rail monitoring system, the computerized communication system, or both, upon detection that the specific individual or any part of the specific individual has crossed over the designated electronic perimeter.

10. The system of claim 9, wherein upon receipt of an alert, the centralized monitoring station is configured to present an audible alert or a visual alert.

11. The system of claim 7, wherein the centralized monitoring station is configured to receive an alert from the computerized virtual safety rail monitoring system, the computerized communication system, or both, upon detection that the specific individual or any part of the specific individual has crossed over the designated electronic perimeter and has failed to return within the designated electronic perimeter within a predetermined period of time.

12. The system of claim 11, wherein upon receipt of an alert, the centralized monitoring station is configured to present an audible alert or a visual alert.

13. The system of claim 1, wherein electronically calibrating virtual safety rails comprises receiving placement information for the virtual safety rails.

14. The system of claim 13, wherein electronically calibrating virtual safety rails comprises allowing a user to draw the virtual safety rails over an image or video from the one or more 3D camera, motion and sound sensors.

15. A system for detecting when a monitored individual or any part of the monitored individual has crossed outside of a designated electronic perimeter, the system comprising:
   a computerized virtual safety rail monitoring system configured to:
      electronically receive a continuous video feed of a room occupied by a specific individual to be monitored;
      electronically recognize one or more biometric identifiers of the specific individual;
      electronically calibrate virtual safety rails defining a designated electronic perimeter within an area of the room; and
      detect whether the specific individual or any part of the specific individual has crossed over the designated electronic perimeter based on 3D information from the continuous video feed received from one or more 3D camera, motion and sound sensors; and a centralized monitoring station configured to receive and display the continuous video feed.

16. The system of claim 15, wherein, upon detecting the specific individual or any part of the specific individual has crossed over the designated electronic perimeter, the computerized virtual safety rail monitoring system is configured to send an alert to the centralized monitoring station, a computerized communication system, or both.

17. The system of claim 16, wherein upon receipt of an alert, the centralized monitoring station is configured to present an audible alert or a visual alert.

18. The system of claim 17, wherein upon receipt of an alert, the centralized monitoring station is configured to move the display of the continuous video feed for which an alert was received from a primary monitoring display to an alert display.

19. The system of claim 16, wherein upon receiving an alert, the computerized communication system is configured to send an electronic notification message of the detected crossing of the designated electronic perimeter to the specific individual, a caregiver, or a designated person.

20. A system for detecting when a monitored individual or any part of the monitored individual has crossed outside of a designated electronic perimeter, the system comprising:

a computerized virtual safety rail monitoring system configured to:

electronically receive a continuous video feed of a room occupied by a specific individual to be monitored;

electronically recognize one or more biometric identifiers of the specific individual;

electronically calibrate virtual safety rails defining a designated electronic perimeter within an area of the room; and detect whether the specific individual or any part of the specific individual has crossed over the designated electronic perimeter based on 3D information from the continuous video feed received from one or more 3D camera, motion and sound sensors;

a centralized monitoring station configured to receive and display the continuous video feed; and a computerized communication system configured to receive an alert from the computerized virtual safety rail monitoring system upon detection that the specific individual or any part of the specific individual has crossed over the designated electronic perimeter, and notify the specific individual, a caregiver, or a designated person.

* * * * *

UNITED STATES PATENT AND TRADEMARK OFFICE
CERTIFICATE OF CORRECTION

PATENT NO. : 10,546,481 B2
APPLICATION NO. : 15/872564
DATED : January 28, 2020
INVENTOR(S) : Neil Kusens Page 1 of 1

It is certified that error appears in the above-identified patent and that said Letters Patent is hereby corrected as shown below:

In the Specification

Column 01, Line 14: Please remove "14/728,762" and replace with --14/084,588--.

Column 02, Line 47: Please remove "time," and replace with --time.--.

Signed and Sealed this
Seventh Day of April, 2020

Andrei Iancu
*Director of the United States Patent and Trademark Office*